United States Patent [19]
Myler

[11] Patent Number: 5,632,762
[45] Date of Patent: May 27, 1997

[54] OSTIAL STENT BALLOON

[75] Inventor: Richard K. Myler, Hillsborough, Calif.

[73] Assignee: Hemodynamics, Inc., San Clemente, Calif.

[21] Appl. No.: 555,523

[22] Filed: Nov. 9, 1995

[51] Int. Cl.$^6$ ........................................... A61M 29/00
[52] U.S. Cl. ........................ 606/194; 606/192; 606/198
[58] Field of Search ............................ 606/191, 192, 606/194, 198; 604/96, 104

[56] References Cited

U.S. PATENT DOCUMENTS

| | | | |
|---|---|---|---|
| 388,510 | 8/1888 | Terrell | 604/96 |
| 4,351,341 | 9/1982 | Goldberg et al. | 604/96 |
| 4,575,371 | 3/1986 | Nordqvist et al. | 604/96 |
| 4,689,041 | 8/1987 | Corday et al. | 604/96 |
| 4,877,031 | 10/1989 | Conway et al. | 604/96 |
| 5,021,045 | 6/1991 | Buckberg et al. | 604/96 |
| 5,061,240 | 10/1991 | Cherian | 604/96 |
| 5,409,495 | 4/1995 | Osborn | 606/194 |
| 5,505,698 | 4/1996 | Booth et al. | 604/96 |

*Primary Examiner*—Michael Buiz
*Assistant Examiner*—Patrick W. Rasche
*Attorney, Agent, or Firm*—Knobbe, Martens, Olson & Bear, LLP

[57] ABSTRACT

Disclosed is a specially tapered balloon such as for sizing an implantable tubular stent that has been positioned within an ostium. In one application of the present invention, a stent is positioned within the right coronary ostium, and the tapered balloon of the present invention is positioned within the stent to provide a radial outward flare on the proximal end of the stent. In this manner, the proximal end of the stent is pressed back against the aortic wall surrounding the right coronary ostium, thereby minimizing any obstruction to blood flow in the aorta, and possibly reducing the risk of restenosis at the right coronary ostium.

15 Claims, 4 Drawing Sheets

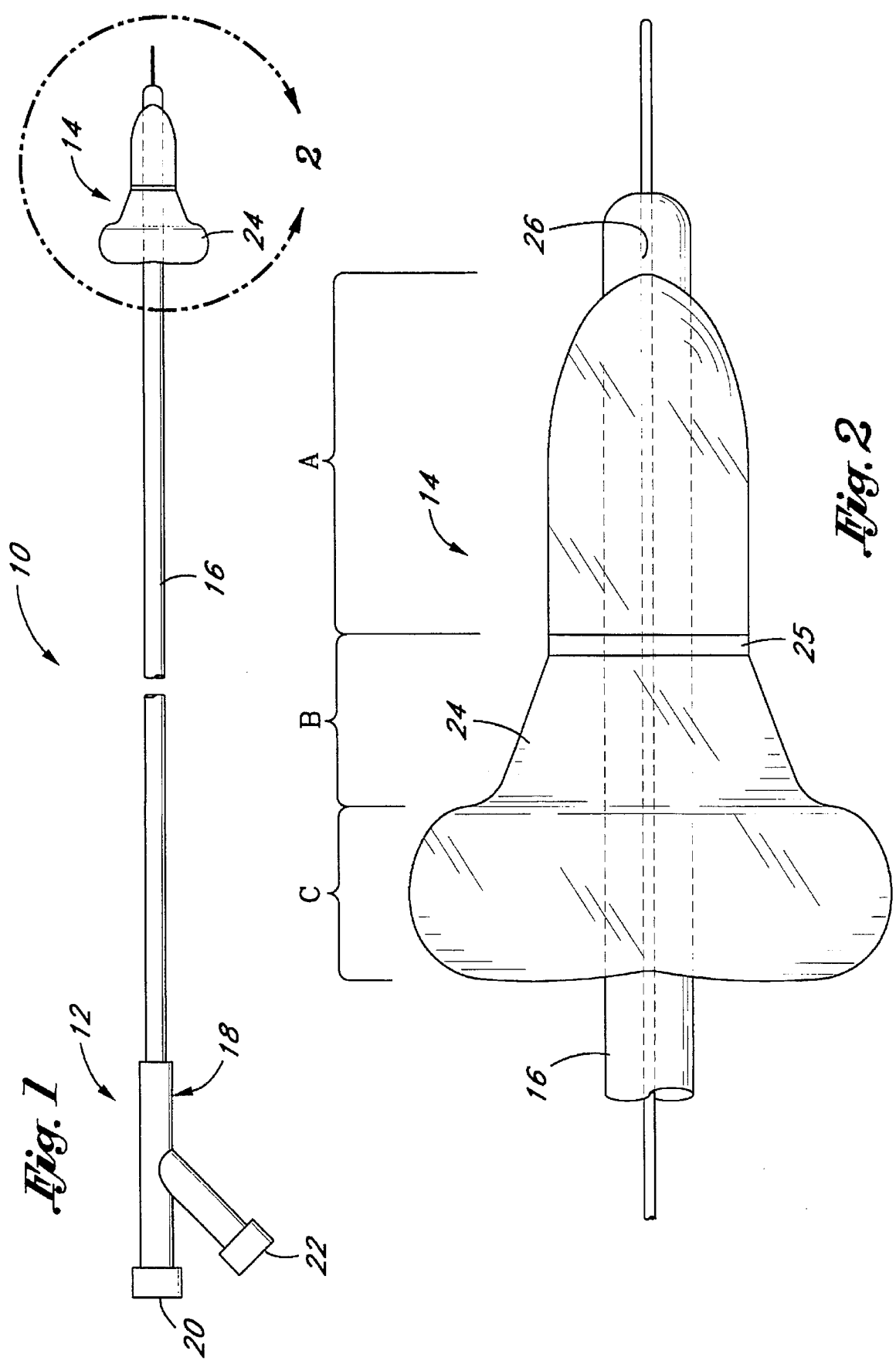

OSTIAL STENT BALLOON

BACKGROUND OF THE INVENTION

The present invention relates generally to balloon dilatation catheters, and, in particular, to a specially configured balloon for implanting and/or sizing an implantable stent at an ostial treatment site.

In a typical percutaneous transluminal coronary angioplasty (PTCA) procedure, a guiding catheter is percutaneously introduced into the patient's cardiovascular system through the brachial or femoral arteries. The guiding catheter is advanced through the patient's vasculature until the distal end is in or near the ostium of the desired coronary artery. A guidewire is thereafter advanced through the guiding catheter and into the patient's coronary vasculature.

A balloon dilatation catheter is thereafter advanced over or along the guidewire until the dilatation balloon is properly positioned within a treatment site. Following positioning of the dilatation catheter, the balloon is inflated to a predetermined size by infusion of an inflation media at relatively high pressures. The inflated balloon radially enlarges the lumen (passage) at the treatment site by compressing the lesion against the artery wall. The balloon is thereafter deflated to a relatively smaller profile, so that the dilatation catheter can be proximally withdrawn from the patient's vasculature and blood flow resumed through the dilated artery.

Some lesions may benefit from deployment of an intravascular prosthesis (stent) immediately after coronary angioplasty to scaffold a flow-limiting dissection, thus obviating the need for emergency coronary artery bypass surgery. Also, certain de novo (new) lesions and some lesions which have developed restenosis may be associated with lower restenosis rates after stent deployment. That is, the risk of restenosis for certain types of lesions can be improved upon by implanting an intravascular prosthesis to maintain vascular patency within the artery at the site of the lesion.

The stent is generally a radially expandable tubular structure, such as a tubular metal mesh, which can be carried to the treatment site on a deflated deployment balloon. The deployment balloon is appropriately positioned within the vessel and inflated to radially outwardly expand the stent against the vessel wall. The deployment balloon can thereafter be deflated and removed from the patient, leaving a radially enlarged tubular stent in place within the treatment site. A variety of expandable tubular stents suitable for use in the coronary artery are known, for example the Palmaz-Schatz stent available from Johnson & Johnson.

Following stent deployment, a second catheter is sometimes positioned within the stent and expanded to accomplish a final "sizing" of the stent within the artery. A variety of stent deployment balloons and stent sizing balloons are known in the art.

Efforts in the deployment balloon and sizing balloon prior art have generally been directed to ensuring a uniform, generally cylindrical inflated profile in the enlarged balloon, so that the stent will be enlarged to a cylindrical final profile. See, for example, U.S. Pat. No. 5,409,495 to Osborn, disclosing a balloon design which is said to eliminate the "problem" of a dog bone-shaped inflated profile in the expanded stent.

Notwithstanding the various efforts in the prior art, the use of cylindrical stents presents some difficulties for treating lesions in certain relatively common locations. For example, in order to treat lesions at or near an arterial branch point, such as the ostium of the right coronary artery, the stent must either project into the aorta or risk not fully covering the proximal portion of the lesion. There remains a need, therefore, for a specialized balloon, designed to inflate or size a previously inflated stent to a specialized inflated profile to treat certain coronary vascular treatment sites.

SUMMARY OF THE INVENTION

There is provided in accordance with one aspect of the present invention a method of shaping an ostial stent. The method comprises the steps of providing an ostial stent balloon catheter of the type having an inflatable balloon, the balloon also having a distal zone with a first inflated diameter and a proximal zone having a second, larger inflated diameter. A stent is located within an ostium at the junction of a main vessel and a branch vessel, such that a distal end of the stent is positioned within the branch vessel and the proximal end of the stent extends into the main vessel. The ostial stent balloon is positioned such that the distal zone on the balloon is positioned within the portion of the stent extending within the branch vessel, and the proximal zone of the balloon is positioned at the proximal end of the stent within the main vessel. The balloon is thereafter inflated to expand the proximal end of the stent radially outwardly in the proximal direction within the main vessel.

Preferably, the positioning stent comprises positioning the distal zone on the balloon within a stent disposed within the right coronary artery, and positioning the proximal zone of the balloon within the aorta. Preferably, the positioning step is accomplished using a guiding catheter, and the method further comprises the steps of applying a pressure on the guiding catheter in the distal direction to further radially flare the proximal end of the stent.

There is provided in accordance with another aspect of the present invention a method of treating an ostial stenosis of the type located at the branch of the right coronary artery and the aorta. The method comprises the steps of dilating the stenosis, and thereafter positioning a tubular vascular prosthesis within the dilated stenosis. A multi-zone balloon is thereafter positioned within the tubular stent, and inflated to expand a distal portion of the tubular stent to a generally cylindrical expanded profile within the right coronary artery, and to expand a proximal portion of the tubular stent to a configuration which is radially outwardly inclined in the proximal direction within the aorta.

In accordance with a further aspect of the present invention, there is provided a balloon dilation catheter adapted for sizing an ostial stent. The catheter comprises an elongate flexible tubular body, having proximal and distal ends. An inflatable balloon is positioned on the distal end of the body, and placed in fluid communication with the proximal end of the catheter by an elongate inflation lumen extending axially therethrough.

The balloon is provided with a proximal zone and a distal zone, and the proximal zone has a larger inflated diameter than the distal zone. Preferably, the proximal zone has an inflated diameter of at least about 2 mm greater than the distal zone. In a preferred embodiment, the distal zone has an axial length of about 50% of the total balloon length, and the proximal zone has an axial length of about 25% of the total balloon length.

Further features and advantages of the present invention will become apparent to those of ordinary skill in the art in view of the detailed description of preferred embodiments which follows when considered together with the attached drawings and claims.

BRIEF DESCRIPTION OF THE DRAWINGS

FIG. 1 is a schematic, side elevational view of a catheter incorporating one embodiment of a balloon of the present invention.

FIG. 2 is an enlarged cross section taken along the lines 2—2 of FIG. 1, showing the profile of the inflated balloon.

DETAILED DESCRIPTION OF THE PREFERRED EMBODIMENT

Figure 3:
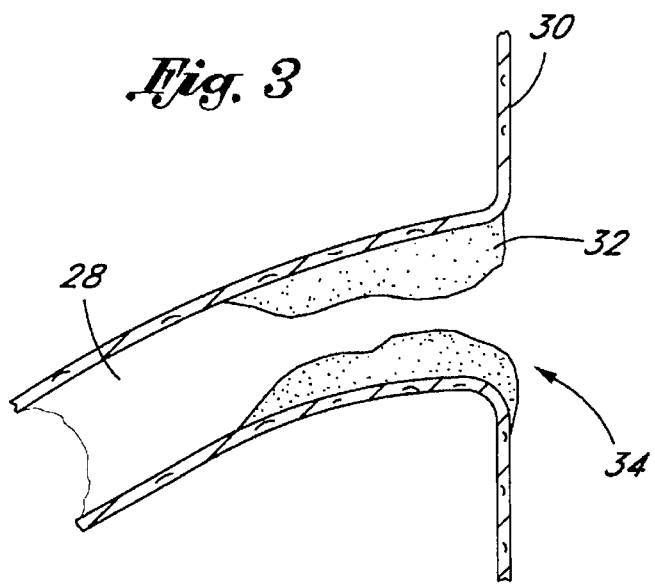
FIG. 3 schematically illustrates a stenosis in the ostium of the right coronary artery.

Referring to FIG. 1, there is disclosed a catheter 10 which carries a balloon 24 in accordance with one aspect of the present invention. The catheter 10 comprises a proximal end 12, a distal end 14, and an elongate flexible tubular body 16 extending therebetween. The tubular body 16 can have any of a variety of lengths well known in the art, such as within the range of from about 110 cm to about 140 cm or otherwise depending upon the intended application.

Proximal end 12 is preferably provided with a manifold 18. In an over-the-wire embodiment, manifold 18 carries a guidewire access port 20 and an inflation port 22 as is well known in the art. In an alternate embodiment configured for rapid exchange or "monorail" use, the proximal guidewire access port 20 is removed from the manifold 18 and positioned along the length of the tubular body 16. Any of a variety of additional access ports can be provided in the manifold as desired, depending upon the intended functionality of the catheter 10.

The distal end 14 of catheter 10 is provided with a balloon 24 configured in accordance with the present invention. In addition, a distal segment of the tubular body 16 is provided with a distal guidewire exit port 26. Guidewire exit port 26 and guidewire port 20 are in communication with each other by way of a guidewire lumen (not illustrated) extending throughout the elongate flexible tubular body 16. In addition, inflation port 22 is in fluid communication with the interior of balloon 24 by way of an elongate inflation lumen (not illustrated) extending through the tubular body 16 as is well known in the art.

The balloon 24 is preferably provided with one or more radiopaque marker bands such as a mid-balloon marker band 25. The construction and possible locations of markers for assisting balloon placement are well known to those of skill in the art. The dimensions, construction materials, and other aspects of the manufacturing and design of catheter 10 are also well understood to those of ordinary skill in the art.

Referring to FIG. 2, there is illustrated an enlarged, cross-sectional view through the balloon 24 in accordance with the present invention. Preferably, balloon 24 is constructed from a relatively noncompliant material such as polyethylene teraphthalate or duralyn. The balloon preferably has a relatively high burst point, such as greater than about 16 atmospheres.

The length of the balloon can be varied depending upon the particular ostial lesion and individual patient characteristics. Generally, the length of the balloon will be within the range of from about 15 to 35 mm, and, preferably, within the range of from about 20 to 30 mm in total length. In one embodiment, the balloon has a length of about 20 mm.

The axial length of the illustrated balloon may be conceptually divided into three segments, illustrated in FIG. 2 as a first segment A, a second Segment B, and a third Segment C. In a balloon 24 having an overall length of about 20 mm, Segment A is preferably about 10 mm in length, Segment B is preferably about 5 mm in length, and Segment C is preferably also about 5 mm in length. However, an overall length of 25 mm (or longer) may be preferable, when deploying a 15 mm stent in an arterial ostial segment.

For example, with a 25 mm long balloon, Segment A would be 50% of the total length (12.5 mm) and Segments B and C, each 25% of the total length (6.25 mm).

The inflated diameters of the proximal, central, and distal segments of the balloon in a series of exemplary embodiments of the present invention are illustrated in Table 1 below. (see p. 8–9)

| DILATED DIAMETERS (mm) | | |
|---|---|---|
| Segment A | Segment B | Segment C |
| 3 | 3.5 | 6 |
| 3.5 | 4.0 | 6.5 |
| 4.0 | 4.5 | 7.0 |
| 4.5 | 5.0 | 7.5 |
| 5.0 | 5.5 | 8.0 |
| 6.0 | 6.5 | 9.0 |
| 7.0 | 7.5 | 10.0 |
| 8.0 | 8.5 | 11.0 |

In general, the proximal end of the balloon will have the largest diameter Segment C. The distal end of Segment A of the balloon 24 comprises a gradual taper such as a conical section from the outside diameter of the tip of tubular body 16 proximally up to the desired inflated diameter of Segment A. Segment A thereafter assumes a relatively cylindrical configuration, which, in use, may approximately match the interior inflated diameter of the stent. At a proximal end of Segment A, the balloon transitions into a second tapered Segment B, which comprises a generally frusto-conical section. Segment b, when inflated, introduces to the implanted tubular stent a generally radially outwardly tapered or flared configuration in the proximal direction.

At the proximal end of Segment B, the diameter of the balloon increases along a relatively steep taper to reach the outside diameter of proximal Segment C. The relatively steep taper between Segments B and C produces a radially outward flare on the proximal end of the tubular stent to flatten the proximal struts of the tubular stent against the aortic wall as will be discussed infra.

The precise configuration of the balloon 24 is not limited to that illustrated, and the balloon need not necessarily be provided with abrupt transitions such as those illustrated between Segments A, B, and C as will be appreciated by one of ordinary skill in the art in view of the disclosure herein. Alternatively, for example, the exterior inflated configuration of the balloon 24 may assume a "smoother" regular increase in outside diameter in the proximal direction, much more like a smooth bell shape. A conical section with or without a radially enlarged proximal base may also be used.

In general, the benefits of the present invention are optimized when the balloon has a larger inflated outside diameter at the proximal end compared to the inflated outside diameter at a distal or intermediate end, so that, when positioned and inflated within the proximal end of an expandable tubular stent, the proximal end of the tubular stent will be provided with a radially outwardly inclined annular flare. Thus, the balloon is preferably provided with at least one annular surface within the working length of the balloon which is inclined radially outwardly in the proximal direction to facilitate a flaring of the proximal portion of the stent.

The method of the present invention can be appreciated by reference to FIGS. 2–8. Referring to FIG. 3, there is illustrated a simplified schematic view of the right coronary artery 28 as it connects to a portion of the aortic wall 30. A stenosis 32 is illustrated in a position at the right coronary ostium 34. Although the present invention will be described in connection with the positioning and sizing of a stent 44 in the right coronary ostium 34, the present invention is equally applicable to any of a variety of other arterial or other vascular branches such as those encountered in the treatment of saphenous vein graft ostial stenoses, renal or aortic arch (subclavian, carotid, innominate) ostial stenoses or other peripheral artery ostial stenoses that will be apparent to those of skill in the art.

Figure 4:
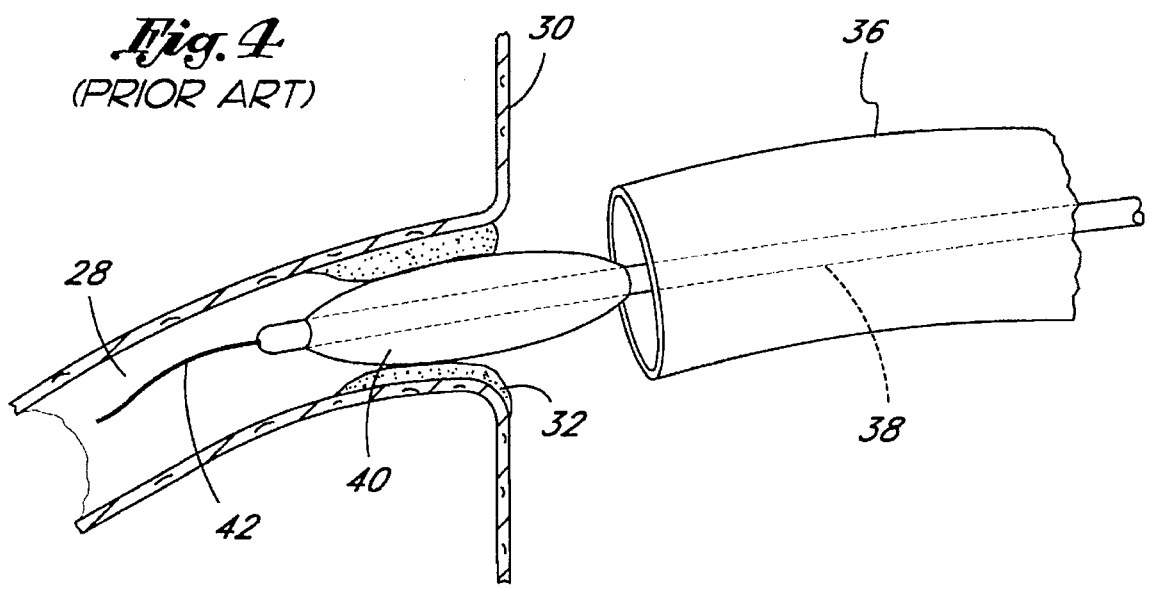
FIG. 4 illustrates a predilatation step using a conventional or high pressure balloon (for pre stent deployment dilation) or other device, such as rotablator or atherocath in the right coronary ostium.

Referring to FIG. 4, a guiding catheter 36 is schematically illustrated within the aorta. In an actual application of the invention, the guiding catheter will extend generally in parallel to the aortic wall 30 as will be appreciated by those of skill in the art. A dilatation catheter 38 has been advanced through the guiding catheter 36 and into position within the stenosis 32. A conventional dilatation balloon 40 is illustrated in an inflated configuration within the stenosis 32. Guidewire 42 projects from the distal end of the dilatation catheter 38 in a conventional manner.

FIG. 4 illustrates a predilatation step, in which the lumen through the stenosis 32 is radially expanded by a conventional or high-pressure dilatation balloon prior to implantation of the stent. Alternatively, any of a variety of other devices, such as a rotablator (rotational atherectomy) or an atherocath, may be substituted for a balloon catheter to predilitate (prepare) the site for a stent. In this version of the procedure, the stent is deployed in a subsequent step, such as that illustrated in FIG. 5. Whether dilatation of the stenosis is accomplished by a dilatation balloon or a new device in advance of stent deployment, is a matter of clinical choice vis-a-vis lesion morphology in view of the capabilities of the available catheters, and does not affect the application of the present invention.

Figure 5:
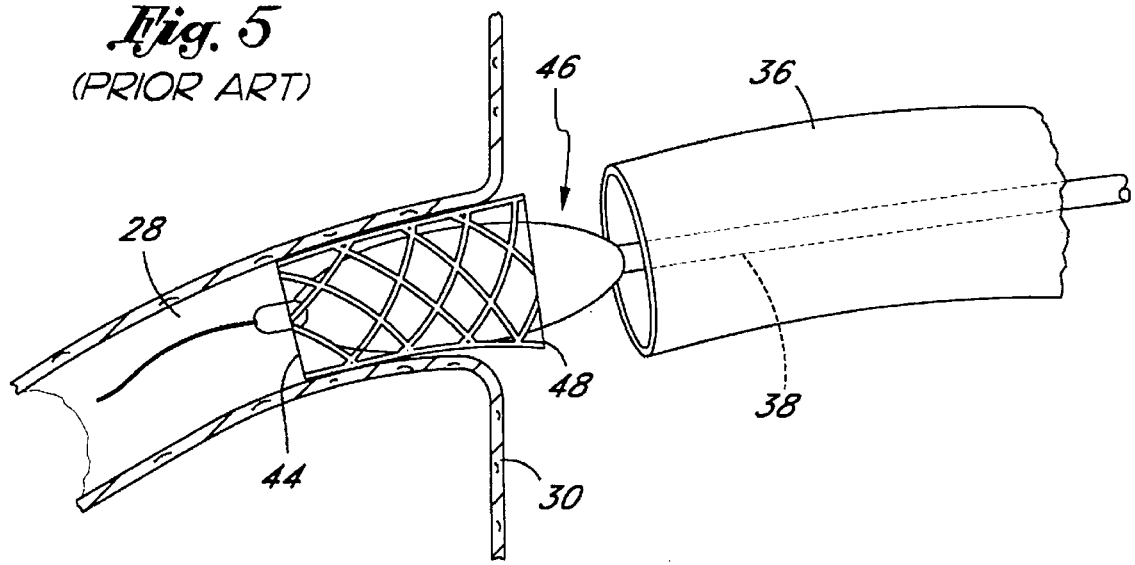
FIG. 5 illustrates deployment of a conventional stent at the treatment site or an unmounted stent crimped on a high pressure balloon such as used in FIG. 4.
Figure 6:
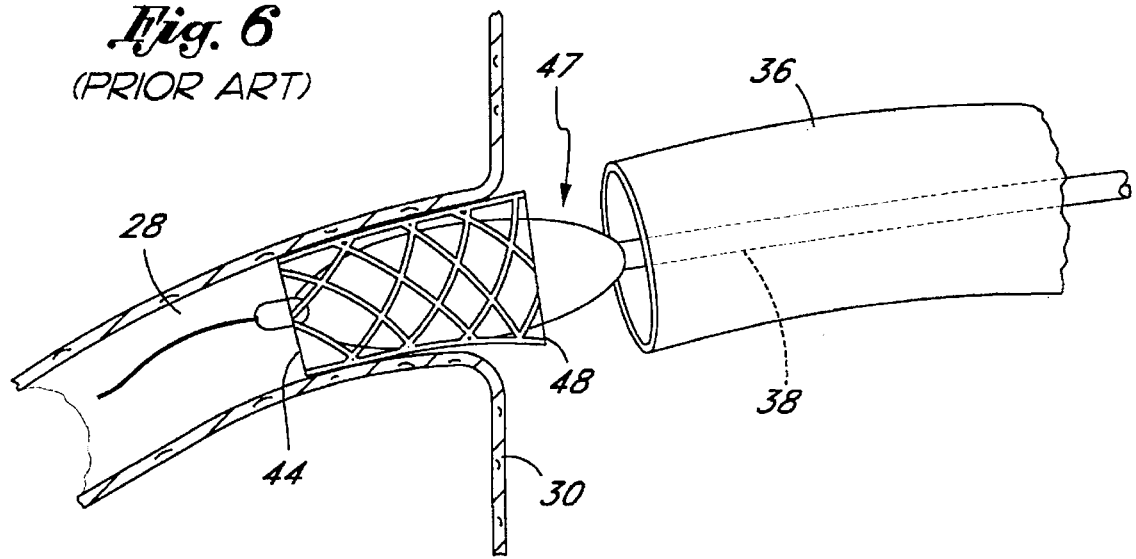
FIG. 6 illustrates a post stent deployment full stent expansion step with a high pressure balloon. This step may be omitted with longer (eg. 25 mm) high pressure inflation or ostial stent balloons.

Referring to FIG. 5, the stent 44 is deployed by a stent deployment balloon 46 following the predilatation step illustrated in FIG. 4. The stent deployment procedure is well known in the art, and, in the illustrated application, involves enlarging the stent to approximately the native interior diameter of the right coronary artery 28.

Presently available stent deployment balloons are generally not used for high pressure enlargement of the stent, and deployment is therefore often followed by insertion of a relatively higher pressure or otherwise different balloon to accomplish a final sizing of the stent within the artery. Thus, following the stent deployment step (illustrated in FIG. 5) the clinician may desire to deflate and withdraw the stent balloon 46 and position and inflate a high-pressure balloon 47 (illustrated in FIG. 6) within the stent prior to use of the balloon catheter of the present invention. (However, unmounted stents could be mounted on the high-pressure balloon used for predilation (FIG. 4)).

By this point in the procedure, the stent 44 has been expanded to an appropriate inside diameter to maintain patency in the right coronary artery 28. A proximal portion 48 of the stent 44 projects out of the right coronary artery 28 and through the right coronary ostium 34 into the aorta.

Figure 7:
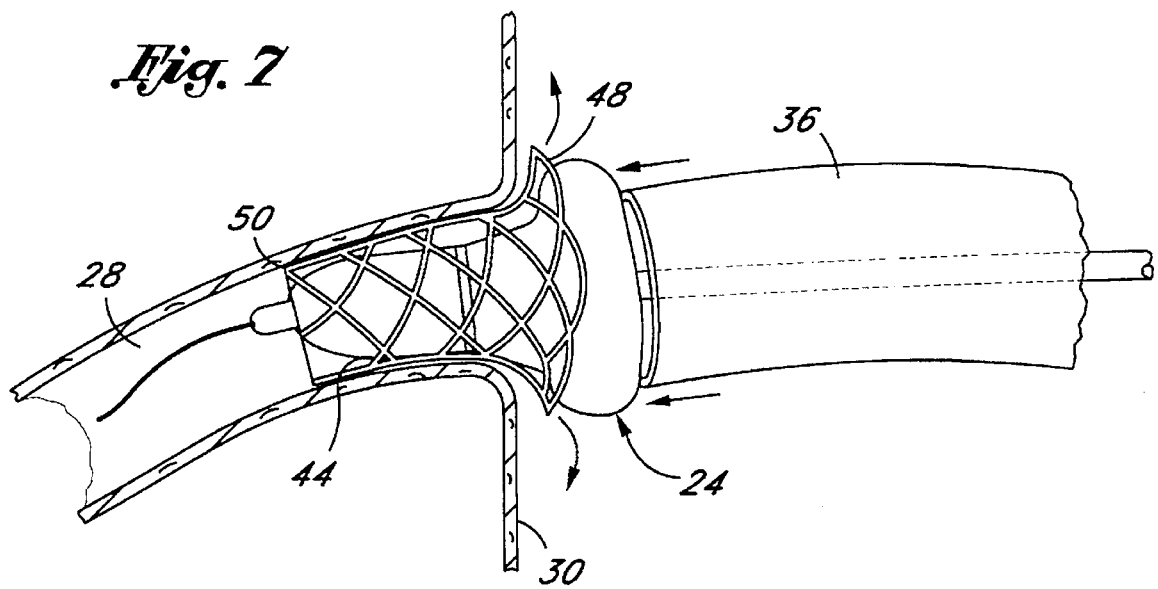
FIG. 7 illustrates a balloon in accordance with the present invention positioned within the implanted stent.

Referring to FIG. 7, there is illustrated a balloon 24 in accordance with the present invention positioned within the stent 44. Inflation of the balloon 24, due to its tapered configuration, inflates the proximal section 48 of the stent 44 into a flared configuration such that the proximal end 48 of the stent 44 inclines radially outwardly in the proximal direction as illustrated schematically in FIG. 7. Due to the preformed inflated configuration of the balloon 24, the distal end 50 of the stent 44 which projects into the right coronary artery 28 is not expanded beyond its desired diameter. On the other hand, the proximal end 48 of stent 44 is flared outwardly and back against the aortic wall 30 to thereby minimize obstruction of the aorta and ostium while at the same time possibly reducing the risk of restenosis in the right coronary ostium 34.

The outer (inflated) diameter of the distal segment (Segment A) varies between 3.0 mm and 8.0 mm. The smaller sizes may be appropriate for native coronary (ostial) stenoses; the mid range sizes appropriate for saphenous vein graft and renal ostial stenoses; and the larger balloons appropriate for subclavian or iliac ostial stenoses. In each balloon, the nominal balloon size is defined by Segment A. In a preferred embodiment, the middle segment (B) has an inflated diameter equal to the inflated diameter of Segment A+0.5 mm. The proximal segment (C) has an inflated diameter equal to the inflated diameter of Segment B+2.5 mm. In general, the proximal segment will be at least about 1 mm, preferably at least about 2 mm and more preferably at least about 2.5 mm greater in diameter than the distal segment. In one embodiment, the proximal segment has an inflated outside diameter of about 3 mm greater than the inflated outside diameter of the distal segment. Following expansion of the balloon 24 of the present invention, the balloon 24 is deflated as is known in the art and catheter 10 is proximally withdrawn from the patient.

Depending upon the force required to radially expand the stent 44, a variety of additional measures may become desirable. In order to accomplish a sufficient radially outwardly flaring of the proximal end 46 of the stent 44, it may become desirable to apply forward axis pressure by the guiding catheter 36, thereby pressing the balloon 24 against the stent to optimize the flared configuration (FIG. 7).

Figure 8:
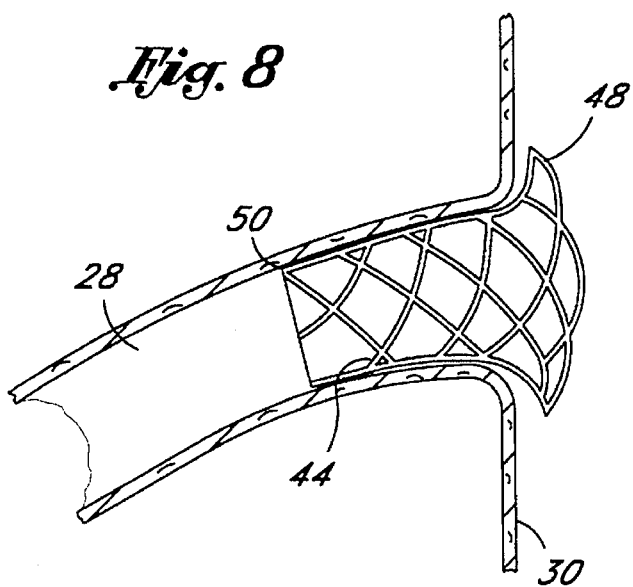
FIG. 8 illustrates the configuration of the implanted stent, following sizing with the balloon of the present invention.

FIG. 8 illustrates the final post-procedural stent deployment position.

Although the present invention has been described in terms of certain preferred embodiments, other embodiments of both the structure and method of the present invention will be apparent to those of skill in the art in view of the disclosure herein and those embodiments are considered to be within the scope of the present claims. For example, different specific configurations of the balloon can be readily envisioned, sharing the common feature that a relatively proximal portion of the balloon has a larger inflated cross-sectional area than a relatively distal portion of the balloon. In addition, the precise manner of conducting the method of the present invention can be varied widely, such as by including additional balloon dilatation and sizing steps, or combining the stent deployment, stent sizing, and stent flaring functions into a single balloon. The scope of the present invention is therefore not intended to be limited by the specific structures and methodologies disclosed herein, but is rather intended to be limited solely by reference to the appended claims.

What is claimed is:

1. A balloon catheter, comprising:

an elongate flexible tubular body, having proximal and distal ends;

an inflatable balloon on the distal end of the body, the inflatable balloon having a total length when inflated;

an inflation lumen extending from the proximal end through the body and in communication with the balloon;

a proximal zone on the balloon; and a generally cylindrical distal zone on the inflated balloon;

wherein the proximal zone flares radially outward such that the proximal zone has a larger inflated diameter than the distal zone.

2. A balloon catheter as in claim 1, wherein the proximal zone has an inflated diameter of least about 2 mm greater than the distal zone.

3. A balloon catheter as in claim 2, wherein the proximal zone has an inflated diameter of about 3 mm greater than the distal zone.

4. A balloon catheter as in claim 2, wherein the axial length of the distal zone is within the range from about 5 mm to about 15 mm.

5. A balloon catheter as in claim 4, wherein the axial length of the distal zone is about 10 mm.

6. A balloon catheter as in claim 5, wherein the axial length of the distal zone is about 12.5 mm.

7. A balloon catheter as in claim 1, wherein the distal zone has an axial length of about 50% of the total balloon length, and the proximal zone has an axial length of at about 25% of the total balloon length.

8. A balloon catheter as in claim 1, further comprising an intermediate zone on the balloon, in between the proximal zone and the distal zone.

9. A balloon catheter as in claim 8, wherein the axial length of the intermediate zone is approximately 25% of the total length of the balloon.

10. A balloon catheter as in claim 8, wherein the distal zone has a generally cylindrical inflated profile over a substantial portion of its length, and the intermediate zone increases in outside diameter in the proximal direction.

11. A method of shaping an ostial stent, comprising the steps of:

providing an ostial stent balloon catheter of the type having an inflatable balloon, said balloon having a distal zone having a first inflated diameter, and a proximal zone having a second, larger inflated diameter;

locating a stent within an ostium at the junction of a main vessel and a branch vessel, such that a distal end of the stent extends into the branch vessel and a proximal end of the stent extends into the main vessel;

positioning the balloon such that the distal zone on the balloon is positioned within the portion of the stent extending within the branch vessel, and the proximal zone of the balloon is positioned at the proximal end of the stent within the main vessel; and inflating the balloon to expand the proximal end of the stent so that the stent flares radially outwardly in the proximal direction within the main vessel.

12. A method as in claim 11, wherein said positioning step comprises positioning the distal zone of the catheter within a stent disposed within the right coronary artery, and positioning the proximal zone of the balloon within the aorta.

13. A method as in claim 11, wherein said positioning step is accomplished using a guiding catheter, and further comprising the step of applying a pressure on the guiding catheter in the distal direction to flare the proximal end of the stent.

14. A method of sizing a stent, comprising the steps of:

positioning an expandable tubular stent in the ostium of a vessel, such that a distal portion of the stent is positioned within a branch vessel, and a proximal portion of the stent is in a main vessel;

dilating a distal portion of the stent to a first diameter within the branch vessel; and dilating a proximal portion of the stent to a second, larger diameter, within the main vessel so as to provide the proximal portion of the stent with a radially outwardly inclined flare in the proximal direction.

15. A method of treating ostial stenosis of the type located at the branch of the right coronary artery and the aorta, comprising the steps of:

dilating the stenosis;

positioning a tubular vascular prosthesis within the dilated stenosis;

positioning a multi-zone balloon within the tubular stent;

inflating the multi-zone balloon within the tubular stent to expand a distal portion of the tubular stent to a generally cylindrical expanded profile within the right coronary artery, and to expand a proximal portion of the tubular stent to a configuration which is flared radially outward in the proximal direction within the aorta.

* * * * *